United States Patent [19]

Wang et al.

[11] Patent Number: 5,294,721
[45] Date of Patent: Mar. 15, 1994

[54] PROCESS FOR THE PREPARATION OF PYRIDINIUM INTERMEDIATES

[75] Inventors: Xiu C. Wang, Park City, Ill.; Panos Kalaritis, New Providence, N.J.; Michelle L. Chang, Vernon Hills, Ill.

[73] Assignee: Abbott Laboratories, Abbott Park, Ill.

[21] Appl. No.: 934,061

[22] Filed: Aug. 21, 1992

[51] Int. Cl.$^5$ ............................................. C07D 213/90
[52] U.S. Cl. ............................................. 546/347
[58] Field of Search ........................ 546/347; 564/441

[56] References Cited

U.S. PATENT DOCUMENTS 4,730,000  3/1988  Chu ..................................... 514/211
4,833,270  5/1989  Bitha et al. .......................... 564/194

OTHER PUBLICATIONS

March, *Advanced Organic Chemistry*, 2nd Edition 1985 pp. 485-489.

*Primary Examiner*—Alan L. Rotman
*Assistant Examiner*—Zinna N. Davis
*Attorney, Agent, or Firm*—Andreas M. Danckers

[57] ABSTRACT

A process for the preparation of halobenzoic acids, comprising the step of reacting a halonitrobenzene with a pyridinium salt to form an intermediate of the formula

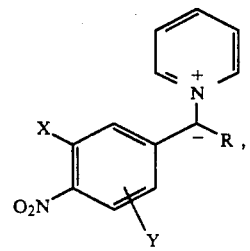

wherein R is selected from the group consisting of hydrogen, alkyl, aryl, alkenyl, alkynyl, —CN, —COOR' and —COR' where R' is alkyl or aryl; X is chloro or fluoro; Y is hydrogen, chloro or fluoro; and Z is chloro, bromo or iodo.

11 Claims, No Drawings

PROCESS FOR THE PREPARATION OF PYRIDINIUM INTERMEDIATES

TECHNICAL FIELD

The present invention relates to the preparation of starting materials for use in the synthesis of quinolone antibacterial agents. More particularly, the invention relates to an improved process for preparing 2-chloro-4,5-difluorobenzoic and 2,4,5-trifluorobenzoic acids by selective nucleophilic substitution of halonitrobenzenes.

BACKGROUND OF THE INVENTION

Halo-substituted 1,4-dihydro-4-oxo-quinoline-3-carboxylic acid derivatives and their corresponding naphthyridines (hereinafter quinolones) are known to be effective antibacterial agents for human and animal use (see, for example, U.S. Pat. No. 4,730,000). Typical starting materials used in the synthesis of such quinolones include halo-substituted benzoic acids and their corresponding esters and acetophenones. It has been found, however, that known methods of preparing these compounds suffer from a number of drawbacks, including the need for expensive or hard-to-obtain reagents; materials hazards such as those associated with the use and decomposition of diazonium salts; and reactions having commercially undesirable selectives and/or yields.

In particular, 2-chloro-4,5-difluorobenzoic acid (CDFBA), 2,4,5-trifluorobenzoic acid (TFBA) and their respective analogous acetophenones are advantageous starting materials for quinolone synthesis. Preparations of these compounds have been described in U.S. Pat. No. 4,833,270, issued May 28, 1989, and in the German Laid-Open Patent Application DE 38 40 371, published May 31, 1990. There remains, however, a need for a process offering an improved means of obtaining these and related quinolone precursors.

SUMMARY OF THE INVENTION

Accordingly, a new process is disclosed for the preparation of halobenzoic acids, and especially CDFBA and TFBA, from halonitrobenzenes, which are relatively inexpensive and are readily available. In one aspect of the present invention is disclosed a method for preparing halobenzoic acids which comprises the step of reacting a halonitrobenzene of the formula

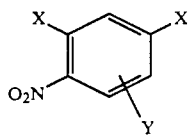

with a pyridinium salt of the formula

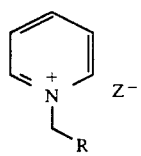

to form an intermediate of the formula

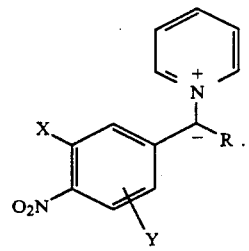

In the above formulae, R may be hydrogen, alkyl, aryl, alkenyl, alkynyl, —CN, —COOR' or —COR' where R' is alkyl or aryl; X may be chloro or fluoro; Y may be hydrogen, chloro or fluoro; and Z may be chloro, bromo or iodo. Preferred embodiments of this inventive aspect include the process in which the halobenzoic acid is 5-chloro-2,4-difluoronitrobenzoic acid or 2,4,5-trifluorobenzoic acid; the process in which the halonitrobenzene is 5-chloro-2,4-difluoronitrobenzene; the process in which R is —COOR' where R' is methyl or ethyl; and the process in which Z is chloro.

In a second aspect of the present invention, the above process comprises the additional step of reacting the intermediate with an oxidant to form a halonitrobenzoic acid of the formula

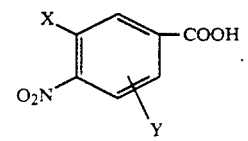

The oxidant is preferably HNO₃, sodium hypochlorite, calcium hypochlorite or potassium permanganate, while the preferred halonitrobenzoic acid is 2-chloro-5-fluoro-4-nitrobenzoic acid.

In a further aspect of the present invention, the process comprises yet another step in which the halonitrobenzoic acid is selectively fluorodenitrated to form a benzoic acid of the formula

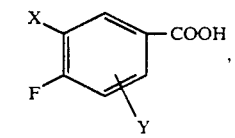

preferably 2-chloro-4,5-difluorobenzoic acid. Moreover, when X and/or Y are chloro, the halobenzoic acid can be more completely fluorinated to form the corresponding di- or trifluorobenzoic acid, preferably 2,4,5-trifluorobenzoic acid.

Also comprised by the present invention are novel synthetic intermediates useful in the above inventive method, having the formula

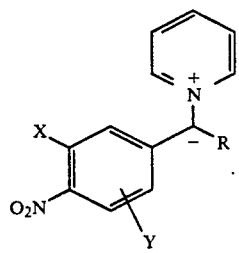

In the above formula, R, X and Y are as previously defined. Preferably, R is —COOR' where R' is methyl or ethyl; X is fluoro; and/or Y is chloro.

DETAILED DESCRIPTION OF THE INVENTION

The term "alkenyl" as used herein refers to an alkyl group as defined below, having at least one carbon-carbon double bond.

The term "alkoxide" as used herein refers to a group of the formula —OR" where R" is an alkyl group as defined below.

The term "alkyl" as used herein refers to a straight- or branched-chain, saturated hydrocarbon radical of one to ten carbon atoms including, but not limited to, methyl, ethyl, propyl, isopropyl, n-butyl, sec-butyl and tert-butyl.

The term "alkynyl" as used herein refers to an alkyl group as defined above, having at least one carbon-carbon triple bond.

The term "aryl" as used herein refers to a cyclic or fused bicyclic, aromatic hydrocarbon radical such as phenyl or naphthyl.

The process of the present invention will be better understood in connection with the following reaction scheme, in which a preferred example of the preparation of trihalobenzoic acids is described. As shown in Scheme I, 5-chloro-2,4-difluoronitrobenzene (I) may be reacted with a pyridinium salt (II or III) in the presence of base to form a para-nitropyridinium-2-oxoalkylide intermediate (IV or V). Suitable bases include diazabicycloundecene (DBU) and potassium, lithium or sodium hydroxides, carbonates or alkoxides. Surprisingly, the reaction occurs only para to the nitro group (>98%, per NMR analysis), and not in the ortho position normally favored by the electron-withdrawing effect of that functionality. While not intending to be limited by theory, it is believed that the para substitution results from steric hindrance of the nitro group to both the incoming nucleophile and the substituent in the transition state.

The pyridinium ylide intermediate (IV or V) is then oxidized to form the corresponding halonitrobenzoic acid (VI). Oxidation may be accomplished by treatment with nitric acid (50% or concentrated), sodium hypochlorite, calcium hypochlorite or other suitable oxidant. Finally, fluorodenitration and, optionally, fluorodechlorination are carried out to convert the nitrobenzoic acid (VI) to 2-chloro-4,5-difluorobenzoic acid (VII) or 2,4,5-trifluorobenzoic acid (VIII). Denitration and dechlorination may be done with potassium fluoride, preferably in the presence of a nitrite scavenger such as phthyloyl dichloride (PDC) or benzene- or toluenesulfonyl chloride in TMSO$_2$. When 2,4,5-trifluorobenzoic acid is being produced, the reaction is carried out at a higher temperature and with more KF than when 2-chloro-4,5-difluorobenzoic acid is the desired product.

Because of the selectivity of the nucleophilic substitution using pyridinium ylide, the above synthesis does not require the separation of isomeric products as is common after conventional acylation of polyhalonitrobenzenes. The desired product may be isolated simply by precipitation, or by extraction and crystallization.

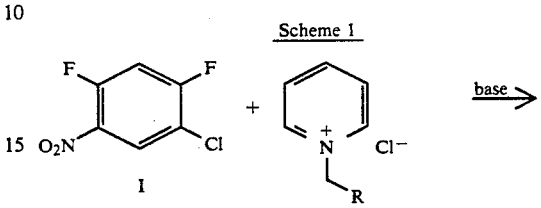

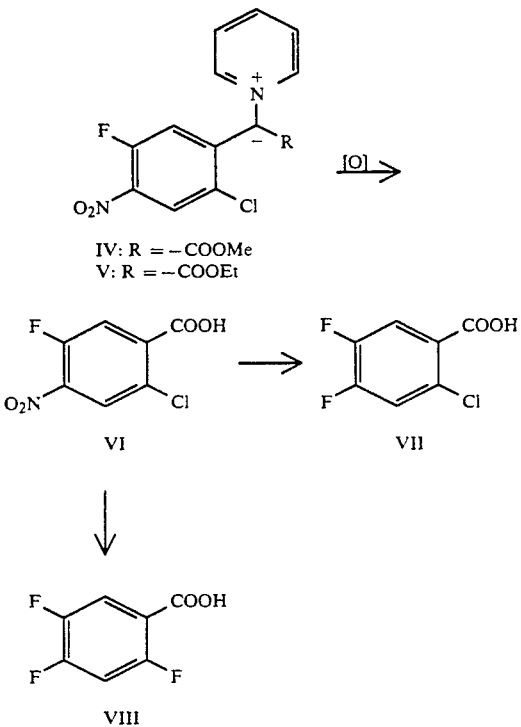

The pyridinium reagents (II or III) and related pyridinium salts are readily prepared. Molar equivalents of pyridine and alkyl (methyl or ethyl) chloroacetate are combined and heated in a suitable solvent, such as ethyl acetate or toluene, to produce the corresponding salt. Other pyridinium reagents of the formula

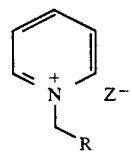

formed by reacting pyridine with the appropriate halide RCH$_2$Z, may also be used in the process of the invention. Suitable halides include those in which Z is chloro, bromo or iodo and R is hydrogen, alkyl, aryl, alkenyl, alkynyl, —CN, —COOR' or —COR' where R' is alkyl or aryl.

The foregoing methods and compounds of the present invention may be better understood by reference to the following Examples, which are provided for illustration and are not intended as a limitation upon the present invention.

EXAMPLE 1

1-(Methoxycarbonylmethyl)pyridinium Chloride (II)

Pyridine (1 equivalent) and methyl chloroacetate (1 equivalent) in ethyl acetate were heated (80° C.) for 24 hours. The reaction mixture was cooled to room temperature and the resulting crystalline pyridinium salt filtered, washed with ethyl acetate, and dried in vacuum.

$^1$H-NMR from DMSO-$d_6$ ($\delta$ ppm): 3.78 (s, 3H), 5.85 (s, 2H), 8.28 (m, 2H), 8.76 (m, 2H), 9.21 (m, 2H).

EXAMPLE 2

1-(Ethoxycarbonylmethyl)pyridinium Chloride (III)

Pyridine (1 equivalent) and ethyl chloroacetate (1 equivalent) in ethyl acetate were heated (70° C.) for 24 hours. The reaction mixture was cooled to room temperature and the resulting crystalline pyridinium salt filtered, washed with ethyl acetate, and dried in vacuum.

$^1$H-NMR from DMSO-$d_6$ ($\delta$ ppm): 1.26 (t, 3H, J=7 Hz), 4.24 (q, 2H), 5.81 (s, 2H), 8.27 (m, 2H), 8.72 (m, 1H), 9.28 (m, 2H).

EXAMPLE 3

Pyridinium Ylide (IV: R=—COOMe)

5-chloro-2,4-fluoronitrobenzene (1.0 equivalent) in DMF ice-bath was treated with the 1-(methoxycarbonylmethyl)pyridinium chloride of Example 1 (1.2 equivalents) followed by potassium hydroxide (2.4 equivalents). The dark-red mixture was stirred at room temperature for 20 hours and poured into cold water ($\sim$5° C.). The resulting dark-red crystals were collected by filtration and dried in vacuum.

$^1$H-NMR from DMSO-$d_6$ ($\delta$ ppm): 3.52 (s, 3H), 7.80 (d, 1H, J=9 Hz), 8.0 (m, 2H), 8.17 (d, 1H, J=17 Hz), 8.42 (m, 1H), 8.91 (m, 2H).

EXPERIMENT 4

Pyridinium Ylide (V: R=—COOEt)

5-chloro-2,4-fluoronitrobenzene (1.0 equivalent) in DMF in ice-bath was treated with the 1-(ethoxycarbonylmethyl)pyridinium chloride of Example 2 (1.2 equivalents) followed by potassium hydroxide (2.4 equivalents). The dark-red mixture was stirred at room temperature for 20 hours and poured into cold water ($\sim$5° C.). The resulting dark-red crystals were collected by filtration and dried in vacuum.

$^1$H-NMR from DMSO-$d_6$ ($\delta$ ppm): 1.08 (t, 3H, J=7 Hz), 4.0 (q, 2H), 7.80 (d, 1H, J=9 Hz), 7.99 (m, 2H), 8.12 (d, 1H, J=17 Hz), 8.44 (m, 1H), 8.91 (m, 1H).

EXAMPLE 5a

2-Chloro-5-fluoro-4-nitrobenzoic acid (VI)

The pyridinium ylide of Example 3 was treated with 50% $HNO_3$ and the mixture heated to 70°-100° C. for 20-48 hours. The mixture was then cooled to 0° C. and the light-yellow precipitate collected by filtration.

EXAMPLE 5b

2-Chloro-5-fluoro-4-nitrobenzoic acid (VI)

The pyridinium ylide of Experiment 2 was dissolved in pyridine and cooled to 0° C. in an ice-bath. An excess of sodium hypochlorite (5%) was added; the mixture was then stirred for 18 hours while being warmed to room temperature during the reaction. Excess bleach was decomposed with saturated aqueous sodium sulfite and the mixture acidified with concentrated HCl. The product was extracted with ethyl acetate. The ethyl acetate layer was washed with brine, dried over sodium sulfate, and condensed to give crude 2-chloro-5-fluoro-4-nitrobenzoic acid which was recrystallized from ethanol-$H_2O$. A light-yellow solid product was obtained.

EXAMPLE 5c

2-Chloro-5-fluoro-4-nitrobenzoic acid (VI)

Calcium hypochlorite (3 equivalents) was suspended in water and cooled in an ice-bath. The pyridinium ylide of Experiment 2 (1 equivalent) was dissolved in dioxane and added to the mixture in small portions. The light yellow mixture was then stirred at room temperature for 2 hours and acidified with concentrated HCl. The named product was isolated by extraction and crystallization as described in Example 5b.

$^1$H-NMR from DMSO-$d_6$ ($\delta$ ppm) for each of Examples 5a, 5b and 5c: 8.01 (d, 1H, J=11 Hz), 8.36 (d, 1H, J=7 Hz), 14.2 (br, 1H).

The above embodiments of the present invention are intended to be illustrative and not restrictive, the scope of the invention being instead defined by the appended claims and equivalencies embraced thereby. It is expected that the particulars of the foregoing description may be readily modified by those skilled in the art without departing from the spirit or essential characteristics thereof.

We claim:

1. A process for the preparation of pyridinium intermediates comprising the step of reacting a halonitrobenzene of the formula

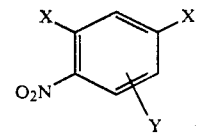

with a pyridinium salt of the formula

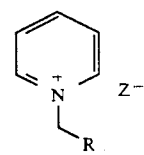

to form a pyridinium intermediate of the formula

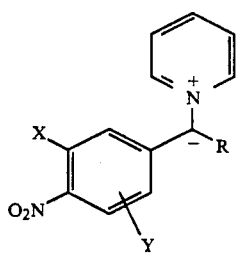

wherein R is selected from the group consisting of hydrogen, $C_1$-to-$C_{10}$ alkyl, $C_2$-to-$C_{10}$ alkenyl, $C_2$-to-$C_{10}$ alkynyl, phenyl, naphthyl, —CN, —COOR', and —COR' where R' is $C_1$-to-$C_{10}$ alkyl, phenyl or naphthyl; X is chloro or fluoro; Y is hydrogen, chloro or fluoro; and Z is chloro, bromo or iodo.

2. A process according to claim 1, wherein R is —COOR' and R' is methyl or ethyl.

3. A process according to claim 1, wherein Z is chloro.

4. A process according to claim 1, wherein the halobenzoic acid is 5-chloro-2,4-difluoronitrobenzoic acid or 2,4,5-trifluorobenzoic acid.

5. A process according to claim 4, wherein the halonitrobenzene is 5-chloro-2,4-difluoronitrobenzene.

6. A process according to claim 1, comprising the additional step of reacting the pyridinium intermediate with an oxidant to form a halonitrobenzoic acid of the formula

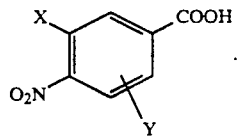

7. A process according to claim 6, wherein the oxidant is selected from the group consisting of $HNO_3$, sodium hypochlorite, calcium hypochlorite and potassium permanganate.

8. A process according to claim 6, wherein the halonitrobenzoic acid is 2-chloro-5-fluoro-4-nitrobenzoic acid.

9. A process according to claim 6, comprising the additional step of fluorodenitrating the halonitrobenzoic acid to form a benzoic acid of the formula

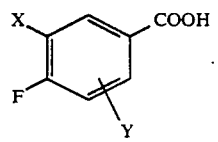

10. A process according to claim 9, wherein the benzoic acid is 2-chloro-4,5-difluorobenzoic acid.

11. A process according to claim 6, comprising the additional step of fluorinating the halonitrobenzoic acid to form 2,4,5-trifluorobenzoic acid.

* * * * *